(12) United States Patent
Min et al.

(10) Patent No.: US 8,090,444 B2
(45) Date of Patent: Jan. 3, 2012

(54) OPTIMIZATION OF CARDIAC PACING THERAPY BASED ON PACED PROPAGATION DELAY

(75) Inventors: Xiaoyi Min, Thousand Oaks, CA (US); Stuart O. Schecter, Great Neck, NY (US)

(73) Assignee: Pacesetter, Inc., Sylmar, CA (US)

( * ) Notice: Subject to any disclaimer, the term of this patent is extended or adjusted under 35 U.S.C. 154(b) by 556 days.

(21) Appl. No.: 12/267,390

(22) Filed: Nov. 7, 2008

(65) Prior Publication Data
US 2010/0121401 A1 May 13, 2010

(51) Int. Cl.
*A61N 1/365* (2006.01)
(52) U.S. Cl. .......................................................... 607/25
(58) Field of Classification Search ................... 607/5, 7, 607/9, 25, 27–28
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,466,254 A | 11/1995 | Helland | |
| 5,476,483 A | 12/1995 | Bornzin et al. | |
| 6,029,088 A | 2/2000 | Budgifvars et al. | |
| 6,152,882 A | 11/2000 | Prutchi | |
| 6,314,323 B1 | 11/2001 | Ekwall | |
| 6,643,549 B1 | 11/2003 | Bradley et al. | |
| 7,206,634 B2 * | 4/2007 | Ding et al. ..................... 607/17 |
| 2005/0043895 A1 | 2/2005 | Schechter | |
| 2005/0149138 A1 | 7/2005 | Min et al. | |

FOREIGN PATENT DOCUMENTS

WO            0042914            7/2000

* cited by examiner

*Primary Examiner* — Scott Getzow
*Assistant Examiner* — Amanda Patton

(57) ABSTRACT

An exemplary method includes delivering stimulation energy via a right ventricular site; sensing an evoked response caused by the delivered stimulation energy at the right ventricular site; calculating a paced propagation delay for the right ventricular site ($PPD_{RV}$); delivering stimulation energy via a left ventricular site; sensing an evoked response caused by the delivered stimulation energy at the left ventricular site; calculating a paced propagation delay for the left ventricular site ($PPD_{LV}$); and determining an interventricular delay time (VV) for delivery of a bi-ventricular pacing therapy based in part on the paced propagation delay for the right ventricular site ($PPD_{RV}$) and the paced propagation delay for the left ventricular site ($PPD_{LV}$). Other exemplary methods, devices, systems, etc., are also disclosed.

19 Claims, 11 Drawing Sheets

OPTIMIZATION OF CARDIAC PACING THERAPY BASED ON PACED PROPAGATION DELAY

TECHNICAL FIELD

Subject matter presented herein generally relates to use of one or more paced propagation delays to optimize cardiac pacing therapies, especially for therapies that include bi-ventricular pacing.

BACKGROUND

Various conditions can damage the myocardium and, in turn, such damage can alter electrical conduction of intrinsic and artificial myocardial stimuli. For example, ischemia can cause myocardial scarring that slows electrical conduction of a pacing stimulus or myocardial depolarization responsive to a pacing stimulus. Hence, after ischemia, a scar may delay depolarization of the myocardium responsive to a pacing stimulus. In this example, a cardiac electrogram may exhibit an increased time interval between delivery of the stimulus and onset of an evoked response or peak of an evoked response. Scarring also occurs when a foreign material such as a pacing lead is introduced into the body. For example, scar tissue at an LV lead can affect characteristics of a cardiac electrogram.

As described herein, various exemplary techniques optionally use one or more paced propagation delays to optimize cardiac pacing, especially where myocardial damage may impair an ability to use one or more alternative optimization techniques.

SUMMARY

An exemplary method includes delivering stimulation energy via a right ventricular site; sensing an evoked response caused by the delivered stimulation energy at the right ventricular site; calculating a paced propagation delay for the right ventricular site ($PPD_{RV}$); delivering stimulation energy via a left ventricular site; sensing an evoked response caused by the delivered stimulation energy at the left ventricular site; calculating a paced propagation delay for the left ventricular site ($PPD_{LV}$); and determining an interventricular delay time (VV) for delivery of a bi-ventricular pacing therapy based in part on the paced propagation delay for the right ventricular site ($PPD_{RV}$) and the paced propagation delay for the left ventricular site ($PPD_{LV}$). Other exemplary methods, devices, systems, etc., are also disclosed.

In general, the various methods, devices, systems, etc., described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
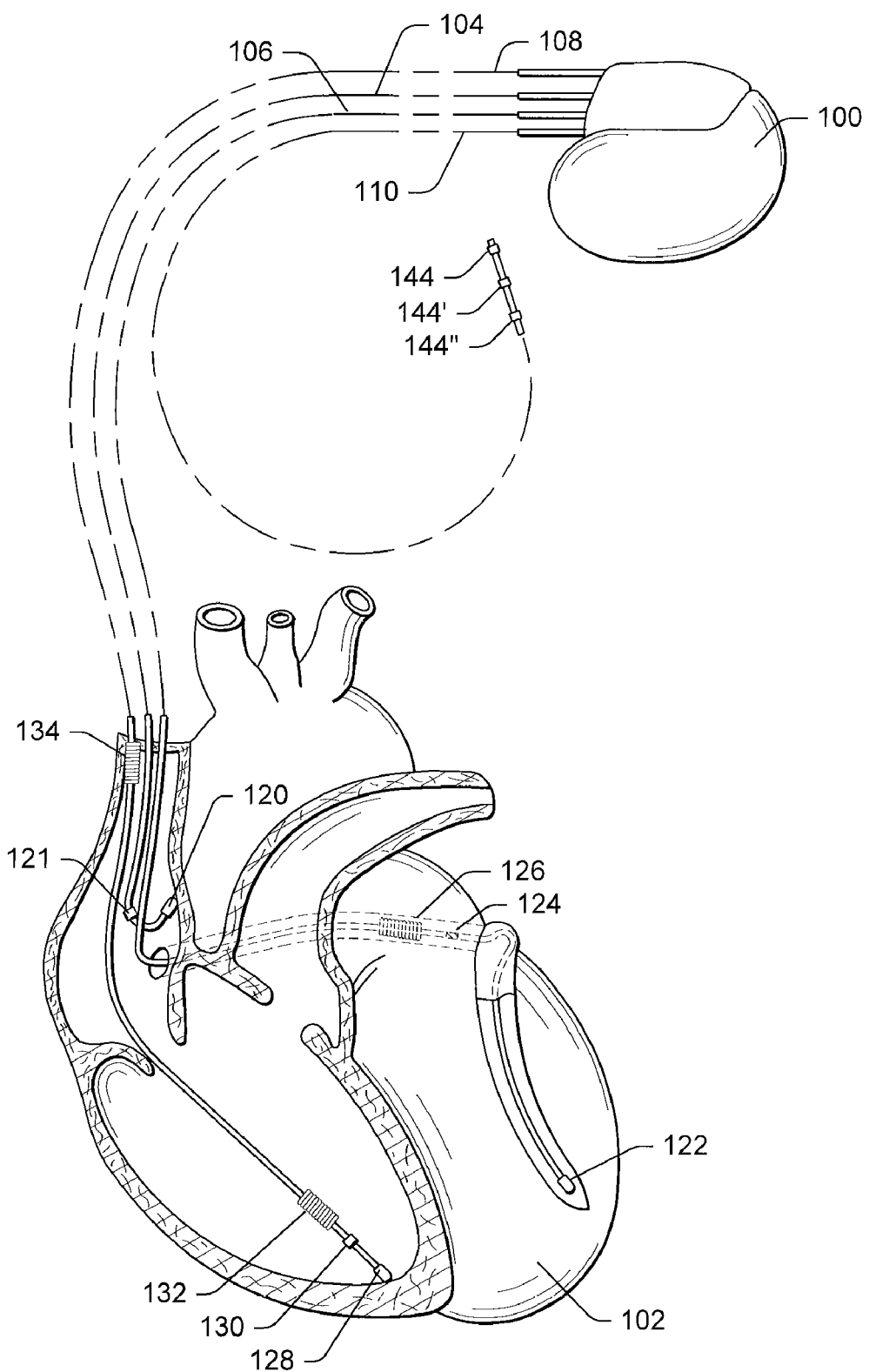
FIG. 1 is a simplified diagram illustrating an exemplary implantable stimulation device in electrical communication with three leads implanted into a patient's heart and another lead; other examples may have different lead arrangements (e.g., different number, placement, type, etc.).

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims.

Overview

Various exemplary methods include two parameters for monitoring patient condition, selecting one or more cardiac therapy parameters, adjusting one or more cardiac therapy parameters, etc. One parameter is referred to as an atrio-ventricular parameter Δ, while the other parameter is referred to as an interventricular conduction delay (IVCD) parameter $\Delta_{IVCD}$.

The atrio-ventricular parameter Δ can be determined in any of a variety of manners. In general, it represents a delay between an event in the right ventricle and the same event in the left ventricle. For example, the parameter Δ may be determined as $AR_{LV}$-$AR_{RV}$ or $PR_{LV}$-$PR_{RV}$ or $R_{LV}$-$R_{RV}$.

The interventricular conduction parameter $\Delta_{IVCD}$ can be determined in any of a variety of manners. In general, it represents a bidirectional difference or a type of conduction hysteresis. For example, it may be determined by delivering a stimulus to the right ventricle, measuring the depolarization in the left ventricle, delivering a stimulus to the left ventricle, measuring the depolarization in the right ventricle and calculating a time difference between the stimulus and measured depolarization in one direction (e.g., right ventricle to left ventricle) and the stimulus and measured depolarization in the other direction (e.g., left ventricle to right ventricle). While this example mentions delivery of a ventricular stimulus, an intrinsic event (e.g., intrinsic atrial) or an atrial stimulus may be noted as the "stimulus" in a ventricle. However, typically this will occur for one direction only (e.g., the ventricle with a faster atrio-ventricular conduction path or paths).

The parameter $\Delta_{IVCD}$ may be referred to as an interventricular conduction delay (IVCD) or a paced interventricular conduction delay (PIVCD).

As an alternative, the parameter $\Delta_{IVCD}$ may be estimated using paced propagation delay information. For example, a paced propagation delay for a right ventricular pacing site ($PPD_{RV}$) and a paced propagation delay for a left ventricular pacing site ($PPD_{LV}$) may be used to estimate a value for the parameter $\Delta_{IVCD}$. Such an estimation technique may be used as an alternative or in addition to foregoing techniques to measure $\Delta_{IVCD}$. In various examples, paced propagation delays can be used where myocardial damage confounds measurement of $\Delta_{IVCD}$. Cardiac electrograms or other information may be used to determine whether damage or other myocardial issues exist that may confound measure of the parameter $\Delta_{IVCD}$.

While various examples pertain to delivering stimulation energy (e.g., a pacing pulse or pulses) to a right ventricular site and to a left ventricular site, various techniques may be used where a pacing therapy involves two right ventricular sites or two left ventricular sites. More generally, various exemplary techniques may be used where two or more stimulation sites are used to achieve optimal contraction of the heart. For example, various techniques may be used to optimize cardiac resynchronization therapy (CRT).

The parameters $\Delta$ and $\Delta_{IVCD}$ may be mapped over time where such mapping can help to track patient condition according to any suitable basis. For example, daily excursions or trends, weekly trends, monthly trends, etc., may be mapped. Further, one or more maps may be acquired for various cardiac therapy parameter sets. For example, if pacing energy is increased, a map or a series of maps may indicate how any or all of the three parameters change for the increase in pacing energy.

With respect to bi-ventricular pacing therapy, a VV delay can be determined on the basis of at least one of the two parameters $\Delta$ and $\Delta_{IVCD}$. For example, the equation $VV=\Delta+\Delta_{IVCD}$ may be used or $VV=\alpha(\Delta+\Delta_{IVCD})$ where the parameter $\alpha$ may be determined in any of a variety of manners (e.g., based on echo cardiography information, etc.). The parameters $\Delta$ and $\Delta_{IVCD}$ typically have time units, alternatively, they may be dimensionless or have other units.

Exemplary Stimulation Device

The techniques described below are intended to be implemented in connection with any stimulation device that is configured or configurable to stimulate nerves and/or stimulate and/or shock a patient's heart.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of cardiac or other tissue (e.g., autonomic nerves, other nerves, muscle). Such a lead may be positioned epicardially or at some other location to stimulate other tissue.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. The lead 104 may have other electrodes as well.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

The coronary sinus lead 106 optionally includes electrodes for stimulation of autonomic nerves. For example, an exemplary coronary sinus lead includes pacing electrodes capable of delivering pacing pulses to a patient's left ventricle and at least one electrode capable of stimulating an autonomic nerve (e.g., for control of autonomic tone, etc.).

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Figure 2:
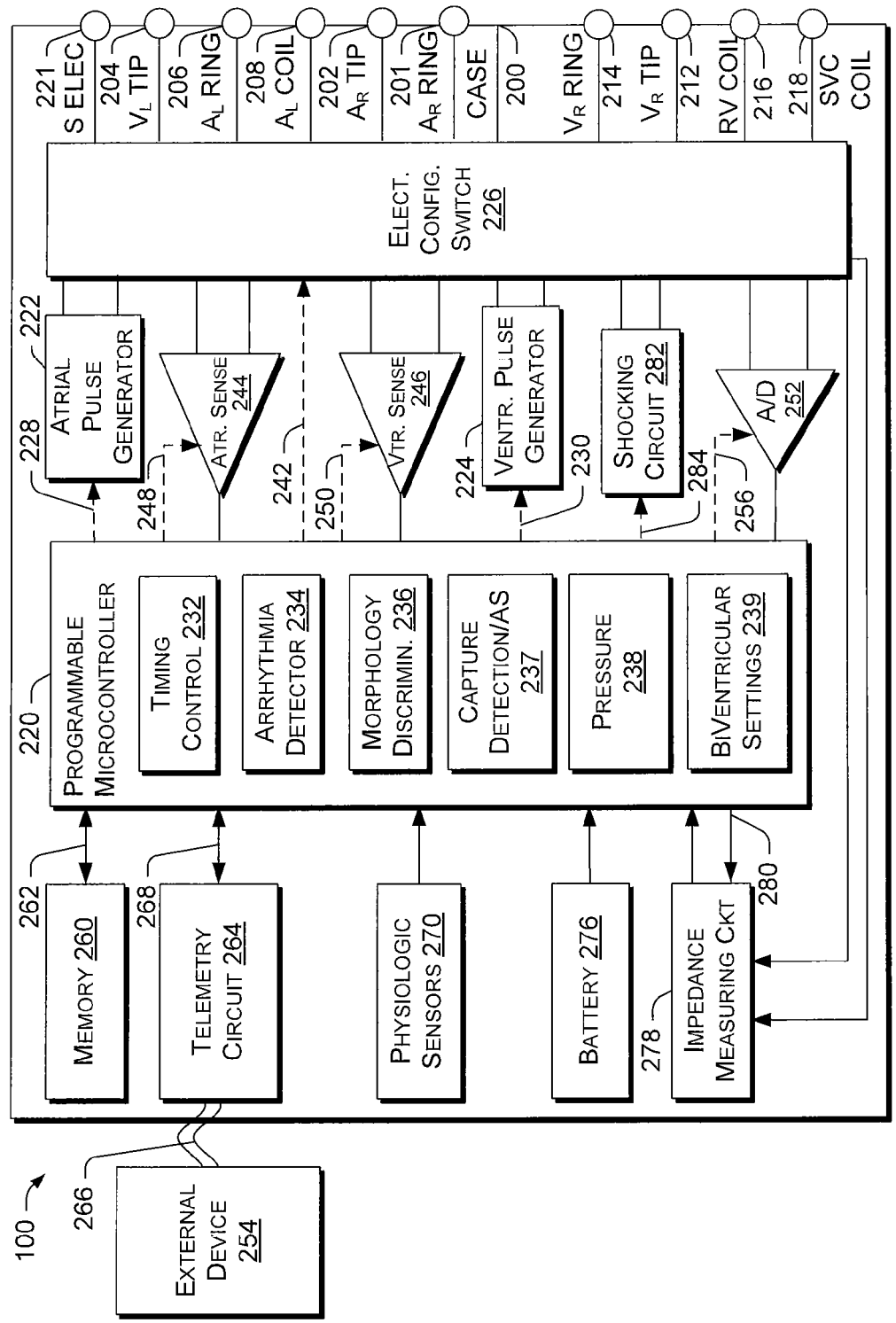
FIG. 2 is a functional block diagram of an exemplary implantable stimulation device illustrating basic elements that are configured to provide cardioversion, defibrillation, pacing stimulation and/or other functions. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. For example, various methods may be implemented on a pacing device suited for single ventricular stimulation and not bi-ventricular stimulation (e.g., single ventricle stimulation at multiple sites). Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar"

modes. Housing 200 may further be used as a return electrode alone or in combination with one or more of the coil electrodes 126,132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable electrodes is also possible via a stimulation terminal S ELEC 221.

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable electrodes is also possible via the stimulation terminal S ELEC 221.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (e.g., PV/AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies. The aforementioned components may be implemented in hardware as part of the microcontroller 220, or as software/firmware instructions programmed into the device and executed on the microcontroller 220 during certain modes of operation.

Microcontroller 220 further includes an AA delay, AV delay and/or VV delay module 238 for performing a variety of tasks related to AA delay, AV delay and/or VV delay. This component can be utilized by the stimulation device 100 for determining desirable times to administer various therapies, including, but not limited to, ventricular stimulation therapy, bi-ventricular stimulation therapy, resynchronization therapy, atrial stimulation therapy, etc. The AA/AV/VV module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays. For example, the module 238 may be configured to measure or acquire paced propagation delay information and decide whether to use such information (e.g., in pacing therapy, determining cardiac condition, etc.).

The microcontroller 220 of FIG. 2 also includes an activity module 239. This module may include control logic for one or more activity related features. For example, the module 239 may include an algorithm for determining patient activity level, calling for an activity test, calling for a change in one or more pacing parameters, etc. These algorithms are described in more detail with respect to the figures. The module 239 may be implemented in hardware as part of the microcontroller 220, or as software/firmware instructions programmed into the device and executed on the microcontroller 220 during certain modes of operation. The module 239 may act cooperatively with the AA/AV/VV module 238.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation) are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGMs) and status information relating to the operation of the device 100 (as contained in the microcontroller 220 or memory 260) to be sent to the external device 254 through an established communication link 266.

The stimulation device 100 can further include one or more physiologic sensors 270. For example, a physiologic sensor may be a "rate-responsive" sensor used to adjust pacing stimulation rate according to activity state of a patient. The one or more physiological sensors 270 may include a sensor to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AA delay, AV delay, VV delay, etc.) at which the atrial and ventricular pulse generators, 222 and 224, generate stimulation pulses.

While shown as being included within the stimulation device 100, it is to be understood that a physiologic sensor may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

The one or more physiological sensors 270 optionally include a minute ventilation sensor (e.g., where minute ventilation is defined as the total volume of air that moves in and out of a patient's lungs in a minute). Signals generated by a sensor can be passed to the microcontroller 220 for analysis in determining whether to adjust the pacing rate, etc. In various configurations, the microcontroller 220 monitors signals for indications of activity status. Where a device includes a position sensor (e.g., accelerometer), the device may determine, for example, whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used. The impedance measuring circuit 278 may be used to acquire impedance information, which may be used in conjunction with paced propagation delay information, deciding whether to acquire paced propagation delay information, etc.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Cardiac Damage: Ischemia, Injury and Infarct

As described herein various exemplary methods may overcome one or more issues associated with cardiac damage. Various methods may be used in instances where a site is located in a damaged region or zone or where a site neighbors or borders a damaged region or zone of the heart.

A bordering zone or border zone may be considered a margin adjacent damaged tissue where a potential for ischemic growth exists. For example, damaged tissue may cause harm neighboring tissue (e.g., chemical release, change in pH, further deterioration in blood flow, etc.). A border zone or margin may have a breadth of about a centimeter or a couple of centimeters from the outer extent of the damaged tissue. To measure or estimate boundaries, various techniques may be used, as explained below.

Figure 3:
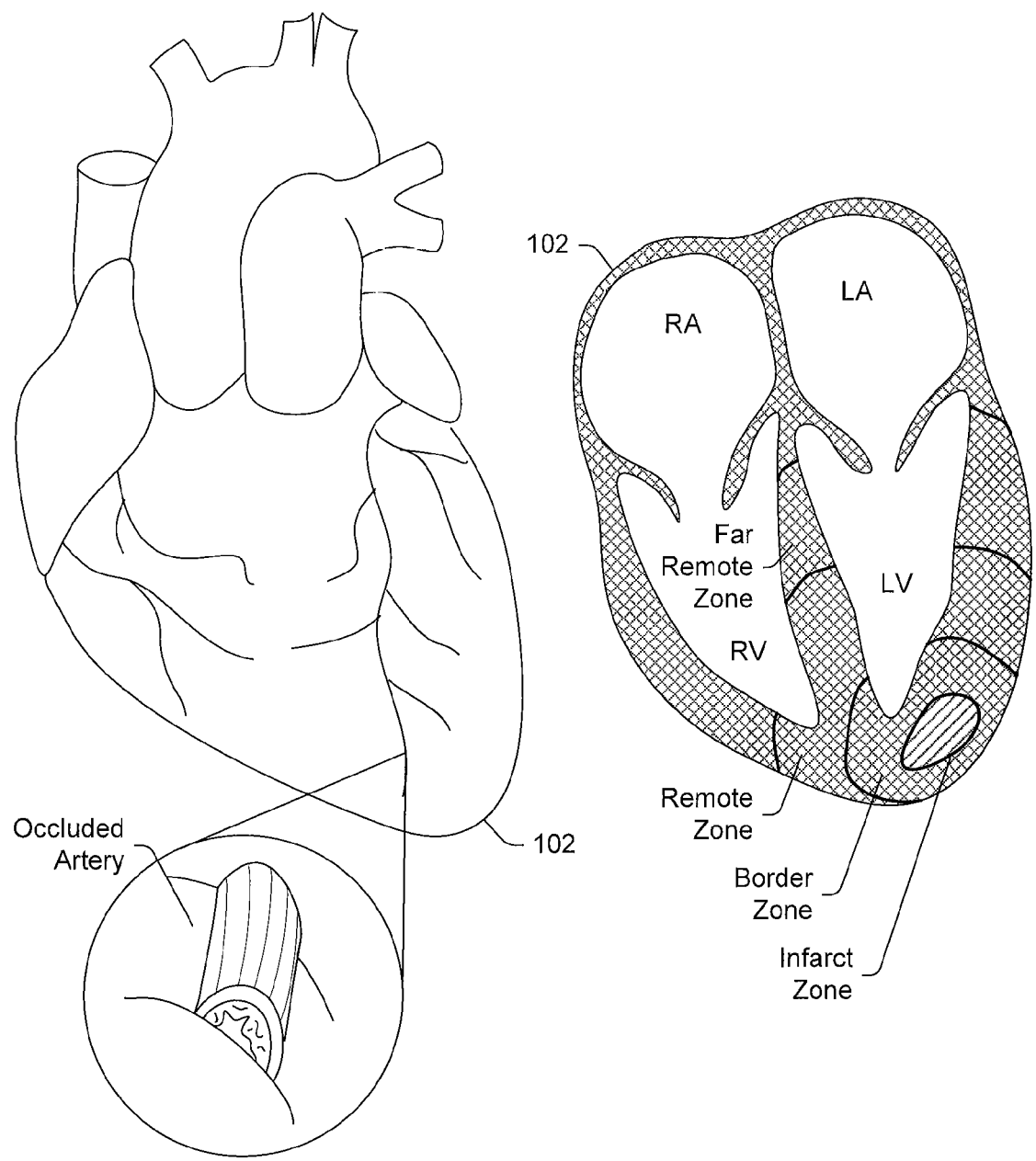
FIG. 3 is a diagram of a heart showing an occluded artery and associated myocardial tissue damage.

To understand better the nature of myocardial damage, FIG. 3 shows a diagram of the heart where an occluded artery causes ischemia, injury and infarct. Insufficient blood supply, due to partial or total occlusion of an artery, to the myocardium can result in myocardial ischemia, injury or infarction, or all three. Occlusion can occur due to atherosclerosis. Atherosclerosis of any of the larger coronary arteries is the most common anatomic condition to diminish coronary blood flow. The branches of coronary arteries arising from the aortic root are distributed on the epicardial surface of the heart. These in turn provide intramural branches that supply the cardiac muscle. Myocardial ischemia generally appears first and is more extensive in the sub-endocardial region since these deeper myocardial layers are farthest from the blood supply, with greater intramural tension and need for oxygen.

More specifically, FIG. 3 shows various epicardial arteries of the heart 102 and a close-up view of an occluded artery that has caused diminished blood supply and an infarct. A cross-sectional view of the heart 102 shows an infarct region or zone, a neighboring border zone, a remote zone and a far remote zone.

With respect to classification of damaged myocardial regions, the International Classification of Diseases, Clinical Modification (ICD-9-CM) has been used to code and classify morbidity data from the inpatient and outpatient records, physician offices, and most National Center for Health Statistics (NCHS) surveys. As described herein, a region, zone or border identified may be optionally classified using one or more of the ICD-9-CM diagnosis codes. For example, ICD-9-CM diagnosis codes include:

- 410.01 (anterolateral wall, acute myocardial infarction-initial episode),
- 410.11 (other anterior wall, acute myocardial infarction-initial episode),
- 410.21 (inferolateral wall, acute myocardial infarction-initial episode), 410.31 (inferoposterior wall, acute myocardial infarction-initial episode), 410.41 (other inferior wall, acute myocardial infarction-initial episode), 410.51 (other lateral wall, acute myocardial infarction-initial episode), 410.61 (true posterior wall, acute myocardial infarction-initial episode), 410.71 (subendocardial, acute myocardial infarction-initial episode), 410.81 (other specified sites, acute myocardial infarction-initial episode) and 410.91 (unspecified site, acute myocardial infarction-initial episode).

While various forms of information may be used to locate damage and/or neighboring tissue, various exemplary methods use cardiac electrograms. A cardiac electrogram may be acquired using electrodes implanted in the body (e.g., subcutaneous, intracardiac, etc.) and/or so-called surface electrodes (e.g., cutaneous electrodes, etc.). In general, a cardiac electrogram acquired using one or more of the former types of electrodes is labeled an EGM while a cardiac electrogram acquired using solely the latter type of electrodes is labeled an ECG. The former group, i.e., EGM, include intracardiac electrograms (IEGMs). In either instance, a cardiac electrogram typically exhibits certain standard features such as a P wave, an R wave, an S wave, a Q wave, a T wave, a QRS complex, etc. Where contraction of a chamber of the heart occurs responsive to delivery of an electrical stimulus, then the electrical waveform may be considered an evoked response (ER) and labeled an A wave, a V wave, etc., depending on the chamber, or chambers, stimulated. Also, an IEGM can include information to determine a paced propagation delay, generally defined as the difference between the delivery time of an electrical stimulus and a feature of an ER caused by the electrical stimulus. In some instances, a paced propagation delay may be defined on another basis, for example, based on a minimum in amplitude for an ER, maximum slope of an ER, etc., as used by an ER detection algorithm.

Various studies have related cardiac electrograms to damage. For example, subendocardial ischemia can prolong local recovery time. Since repolarization normally proceeds in an epicardial-to-endocardial direction, delayed recovery in the subendocardial region due to ischemia does not reverse the direction of repolarization but merely lengthens it. This generally results in a prolonged QT interval or increased amplitude of the T wave or both as recorded by the electrodes overlying, or otherwise sensing activity at, the subendocardial ischemic region.

Subepicardial or transmural ischemia is typically said to exist when ischemia extends subepicardially. This type of damage has a more visible effect on recovery of subepicardial cells compared with subendocardial cells. Recovery is more delayed in the subepicardial layers, and the subendocardial muscle fibers often seem to recover first. Repolarization is endocardial-to-epicardial, resulting in inversion of the T waves in leads overlying, or otherwise sensing activity at, the ischemic regions.

Injury to myocardial cells results when an ischemic process is more severe. Subendocardial injury on a surface ECG (i.e., an ECG) is typically manifested by ST segment depression while, in contrast, subepicardial or transmural injury is manifested as ST segment elevation. In patients with coronary artery disease, ischemia, injury and myocardial infarction of different areas can coexist and produce mixed and complex ECG patterns.

The term infarction describes necrosis or death of myocardial cells. Atherosclerotic heart disease is the most common underlying cause of myocardial infarction. The left ventricle is the predominant site for infarction; however, right ventricular infarction occasionally coexists with infarction of the inferior wall of the left ventricle. The appearance of pathological Q waves is the most characteristic ECG finding of transmural myocardial infarction of the left ventricle. A pathological Q wave is defined as an initial downward deflection of a duration of about 40 ms or more in any lead of a multi-lead surface ECG unit (except lead III and lead aVR). The Q wave appears when the infarcted muscle is electrically inert and the loss of forces normally generated by the infarcted area leaves unbalanced forces of variable magnitude in the opposite direction from a remote region or zone (e.g., an opposite wall). These forces can be represented by a vector directed away from the site of infarction and seen as a negative wave (Q wave) by electrodes overlying, or otherwise sensing activity at, the infarcted region.

During acute myocardial infarction, the central area of necrosis is generally surrounded by an area of injury, which in turn is surrounded by an area of ischemia. Thus, various stages of myocardial damage can coexist. One commonly used distinction between ischemia and necrosis is whether the phenomenon is reversible. Transient myocardial ischemia that produces T wave, and sometimes ST segment abnormalities, can be reversible without producing permanent damage and is not accompanied by serum enzyme elevation.

Two types of myocardial infarction can be typically observed electrocardiographically: Q wave infarction and Non-Q wave infarction. Q wave infarction, which is diagnosed by the presence of pathological Q waves and is also called transmural infarction. However, transmural infarction is not always present, hence, the term Q-wave infarction may be preferable for ECG description. Non-Q wave infarction is typically diagnosed based on the presence of ST depression and T wave abnormalities. Elevation of serum enzymes is expected in both types of infarction. In the absence of enzyme elevation, ST and T wave abnormalities are interpreted usually as due to injury or ischemia rather than infarction.

As already mentioned, a damage site (e.g., ischemia, injury, infarction) can be localized to some extent using cardiac electrograms, for example, the general location of an infarct can be detected by an analysis of a 12-lead ECG. Leads that best detect changes in commonly described locations are classified as follows: Inferior (or diaphragmatic) wall—II, II and aVF; Septal—V1 and V2; Anteroseptal—V1, V2, Vf3 and sometimes V4; Anterior—V3, V4 and sometimes V2; Apical—V3, V4 or both; Lateral—I, aVL, V5 and V6; and Extensive anterior—I, aVL and V1 through V6.

Posterior wall infarction does not typically produce Q wave abnormalities in conventional leads and is generally diagnosed in the presence of tall R waves in V1 and V2. The classic changes of necrosis (Q waves), injury (ST elevation), and ischemia (T wave inversion) may all be seen during acute infarction. In recovery, the ST segment is the earliest change that normalizes, then the T wave; the Q wave usually persists. Therefore, the age of the infarction can be roughly estimated from the appearance of the ST segment and T wave. The presence of the Q wave in the absence of ST and T wave abnormality generally indicates prior or healed infarction. Although the presence of a Q wave with a 40 ms duration is usually sufficient for diagnosis, criteria defining the abnormal depth of Q waves in various leads have been established. For example, in lead I, the abnormal Q wave must be more than 10 percent of QRS amplitude; in leads II and aVF, it should exceed 25 percent; and in aVL it should equal 50 percent of R wave amplitude. Q waves in V2 through V6 are typically considered abnormal if greater than 25 percent of R wave amplitude.

A deep Q wave generally indicates myocardial necrosis, although similar patterns may be produced by other conditions, such as WPW syndrome, connected transportation of the great vessels, etc. ST-segment elevation can be observed in conditions other than acute myocardial infarction.

With respect to ST segment elevation, other causes of ST segment elevation include the following: acute pericarditis (ST elevation in acute pericarditis is generally diffuse and does not follow the pattern of blood supply. As a rule these changes are not accompanied by reciprocal depression of the ST segment in other leads); early repolarization (In some patients without known heart disease, particularly young patients, early takeoff of the ST segment may be seen); ventricular aneurysm (after acute myocardial infarction, the ST segment usually normalizes. However, in the presence of a persistent aneurysm in the region of infarction, ST segment elevation may persist indefinitely).

Abnormal T waves can be seen in a variety of conditions other than myocardial ischemia, including: hyperventilation, cerebrovascular disease, mitral valve prolapse, right or left ventricular hypertrophy, conduction abnormalities (right or left bundle branch block), ventricular preexcitation, myocarditis, electrolyte imbalance, cardioactive drugs such as digitalis and antiarrhythmic agents, or for no obvious cause (particularly in women).

Figure 4:
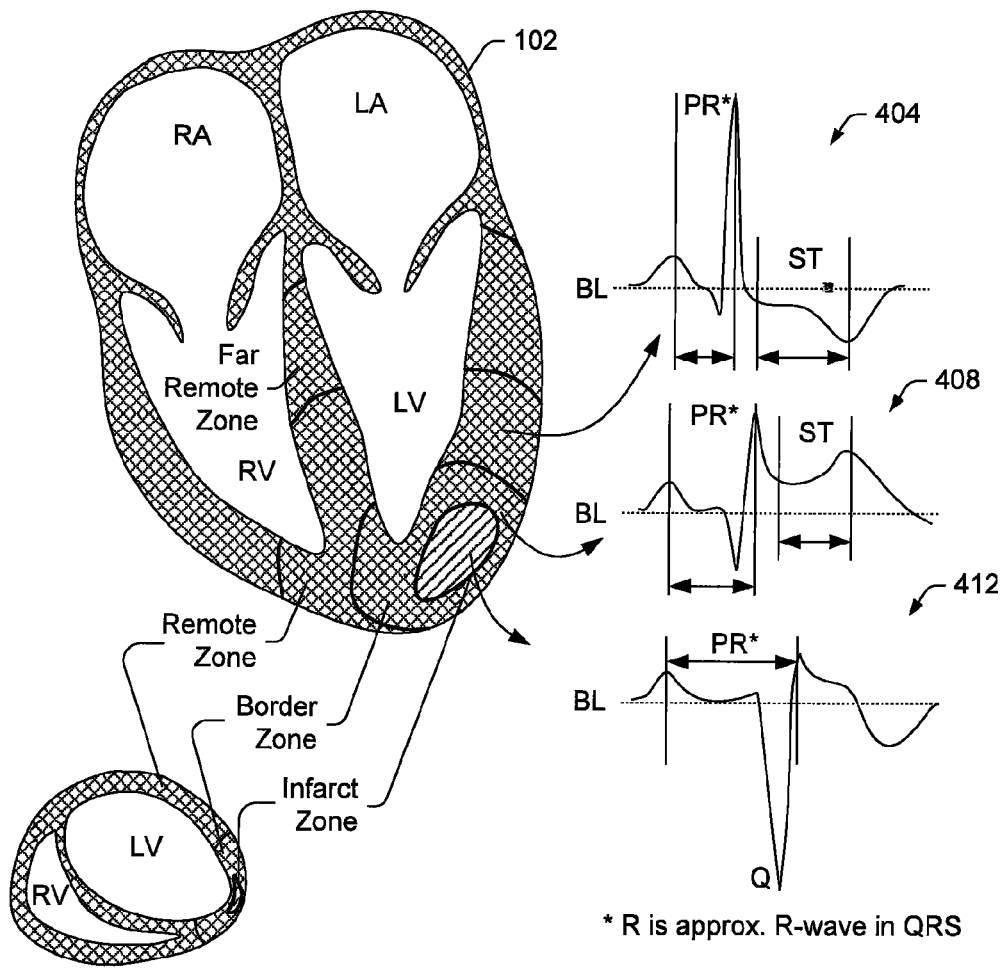
FIG. 4 is a diagram of a heart and cardiac electrograms along with exemplary criteria for assessing cardiac condition.

Thus, cardiac electrograms may provide insight into location, severity, age, repair, etc., of myocardial tissue damage (e.g., ischemia, injury and/or infarct). FIG. 4 shows cardiac infarct and electrical information 400 in the form of two cross-sectional views of the heart 102 along with a series of cardiac electrograms 404, 408, 412 and exemplary criteria 440 for use analyzing one or more cardiac electrograms. In the block 440, the term "J point" refers to the point at which the QRS complex meets the ST wave. Also, for FIG. 4, the R* refers specifically to the R-wave of a QRS complex. In other instances, R refers generally to an intrinsic ventricular event (e.g., ventricular contraction due to AV nodal conduction whether originating from intrinsic or electrically stimulated atrial activity).

The remote zone cardiac electrogram 404 exhibits a depressed ST segment and may represent an ischemic or injured region. The border zone cardiac electrogram 408 exhibits an elevated ST segment and a prolonged PR segment and may represent subepicardial or transmural injury. The infarct zone cardiac electrogram 412 exhibits a deep Q wave, which generally indicates myocardial necrosis, i.e., infarct.

Electrical information may be acquired from patient populations (e.g., prior infarct, heart failure, normal, young, old, etc.) and used for purposes of analyzing electrical information for a particular patient. For example, electrical information for healthy patients may be used to establish one or more standard segments (e.g., standard time for ST segment, standard amplitude for ST, Q, PR, etc.). One or more of such standards may then be used to assess cardiac condition of a particular patient. In a specific example, PR and ST interval times are acquired for a patient and compared to standard PR and ST interval times. The comparison may be a ratio based comparison (e.g., PR/ST, ST/PR, etc.), a percentage based comparison, etc., where the comparison can help assess a region of the patient's heart with respect to an infarct (e.g., distance of region from an infarct zone, damage level, etc.).

Various exemplary methods include acquiring one or more cardiac electrograms and analyzing the one or more cardiac electrograms to determine health of a myocardial region.

Figure 5:
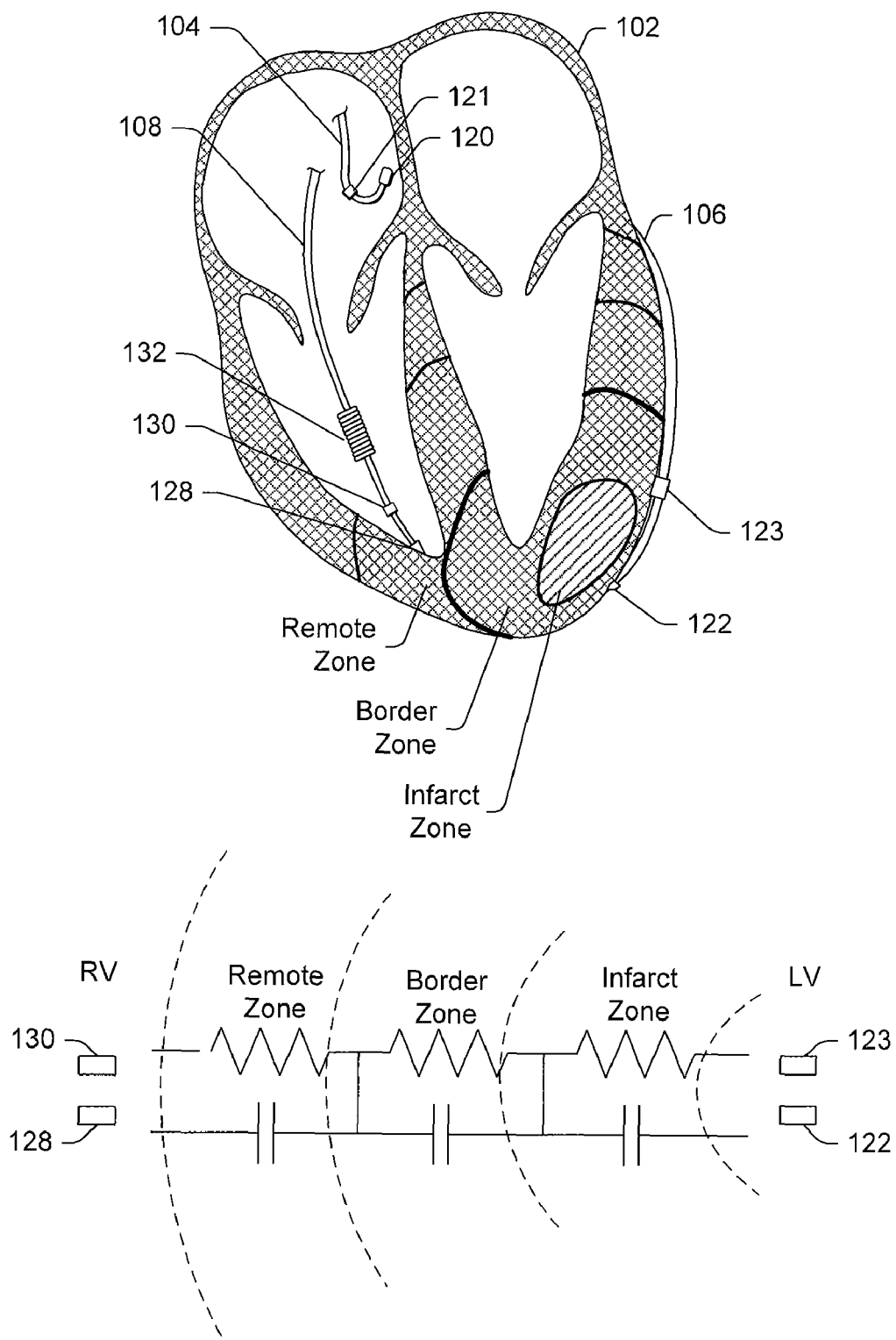
FIG. 5 is a diagram of a heart and various leads where the heart includes an infarct zone as a damaged region.

FIG. 5 shows a diagram of cardiac damage and conduction 500. The heart 102 is shown with various zones, a right atrial lead 104, a left ventricular lead 106 and a right ventricular lead 108. Conduction is illustrated in a circuit diagram where the various zone have respective conduction properties. For example, energy delivered using the tip electrode 122 and the ring electrode 123 of the left ventricular lead 108 travels through the infarct zone, the border zone and the remote zone to electrodes 128 and 130 of the right ventricular lead, which are configured for sensing. The energy delivered may cause an evoked response, which, in turn, can be sensed locally (e.g., by the left ventricular lead) and/or remotely (e.g., by the right ventricular lead). As discussed below, local sensing of an evoked response can provide pacing delay information whereas remote sensing is used for sensing interventricular conduction delay information.

With respect to measurement of interventricular conduction delays, the conduction time from a site in the left ventricle to a site in the right ventricle (IVCD-LR) may differ from the conduction time for the site in the right ventricle to the site in the left ventricle (IVCD-RL). For example, consider the electrode 122 as being located near an infarct zone, which may introduce delays for sensing and delivery of energy that contribute to a difference between IVCD-RL and IVCD-LR.

As described herein, circumstances may exist where a value for the parameter $\Delta_{IVCD}$ cannot be readily determined. For example, consider the situation where the atrial lead 104 delivers an atrial pulse that causes an atrial evoked response (A-wave) and intrinsic conduction of the resulting wavefront causes the left ventricle to contract ($R_{LV}$), characterized by the delay $AR_{LV}$, and causes the right ventricle to contract ($R_{RV}$), characterized by the delay $AR_{RV}$. To measure IVCD-LR, there should be adequate time for wavefront propagation from the left ventricle to the right ventricle without interference from intrinsic conduction to the right ventricle. In other words, if the delivery of energy to the left ventricle occurs at about the time of an atrial pace, the time IVCD-LR should be less than the time $AR_{RV}$. Whether this criterion is met depends largely on the condition of the tissue in the left ventricle; noting that the $AR_{RV}$ delay indicates with some certainty the condition of the pathway from the right atrium to the right ventricle. Hence, in situation where the left ventricular site is at or near a damaged region of the heart, circumstances may confound measurement of IVCD-LR and hence the parameter $\Delta_{IVCD}$. When such circumstances exist, paced propagation delay information may be used to estimate $\Delta_{IVCD}$.

Figure 6:
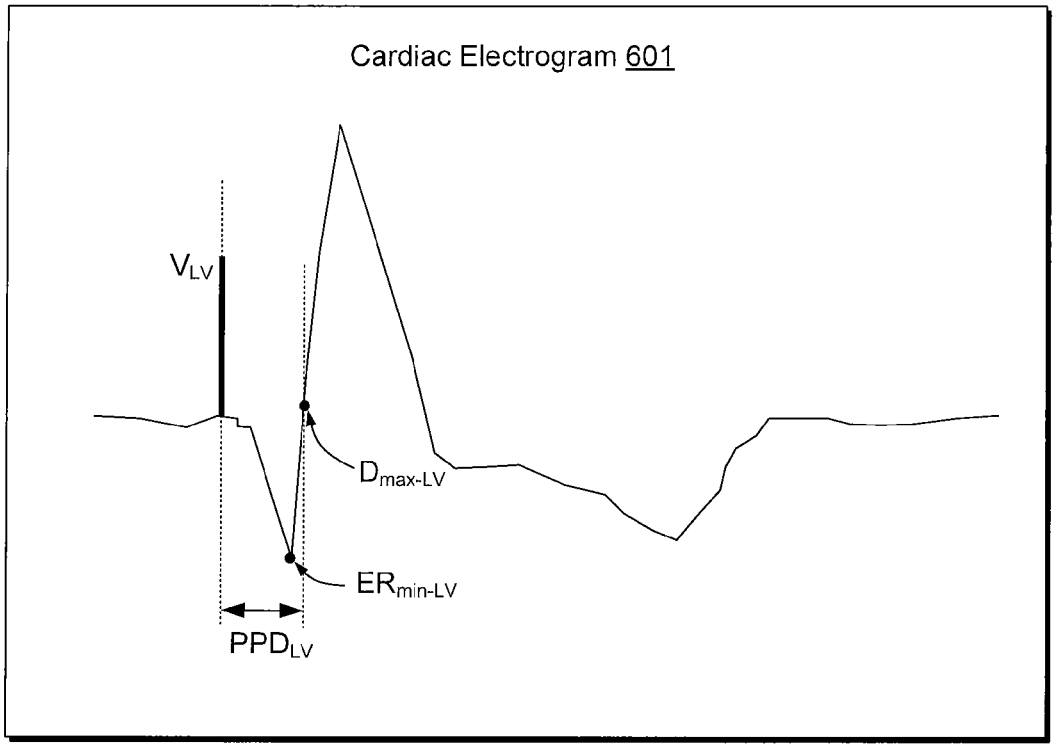
FIG. 6 is a diagram of an exemplary assessment technique for determining a paced propagation delay.

FIG. 6 shows an exemplary technique 600 for measuring paced propagation delay. In this example, a cardiac electrogram 601 shows a waveform for a pulse to the left ventricle ($V_{LV}$) and a waveform of a corresponding evoked response ($ER_{LV}$). A time interval referred to as a paced propagation delay (PPD) may be considered a "travel" time for a wavefront and may be measured from a delivery time of a stimulus to a feature time as sensed on a wavefront resulting from the stimulus (e.g., a feature of an evoked response). In FIG. 6, the paced propagation delay ($PPD_{LV}$) is measured from a delivery time of the left ventricular stimulus to a maximum positive slope of the corresponding evoked response in the left ventricle ($D_{max-LV}$). Sensing polarity or other factors may be considered when selecting an appropriate feature for measurement of a PPD (e.g., a reversal in sensing polarity would result in a waveform inverted from that of FIG. 6). In another example, a PPD may be equivalent to a pacing latency where it is measured as the difference between the time of delivery of a stimulus to deviation of a signal from a baseline value (e.g., onset of an evoked response). In yet another example, a PPD may be measured as the difference between the time of delivery of a stimulus to a minimum or maximum signal amplitude of an evoked response (e.g., $ER_{min-LV}$).

As described herein, a PPD is site specific in that a PPD for one ventricular stimulation site may differ from that of another ventricular stimulation site. As mentioned, in the example of FIG. 6, PPD for the left ventricle ($PPD_{LV}$) is given as $D_{max\ LV}$-$V_{LV}$. Similarly, a PPD may be acquired for the right ventricle ($PPD_{RV}$); noting that another left ventricular site, etc., could be used depending on the nature of the pacing therapy and lead and electrode configuration.

FIG. 6 also shows some cardiac information 603. The information 603 includes PR, PPD and IVCD times for the left ventricle and for the right ventricle. As indicated, the difference between the left and right ventricular PPDs (ΔPPD) may be used as an estimate for the difference between the IVCD-LR and IVCD-RL ($\Delta_{IVCD}$). A PPD assessment may be used when IVCD-LR and/or IVCD-RL cannot be accurately measured (e.g., due to conduction problems).

Figure 7:
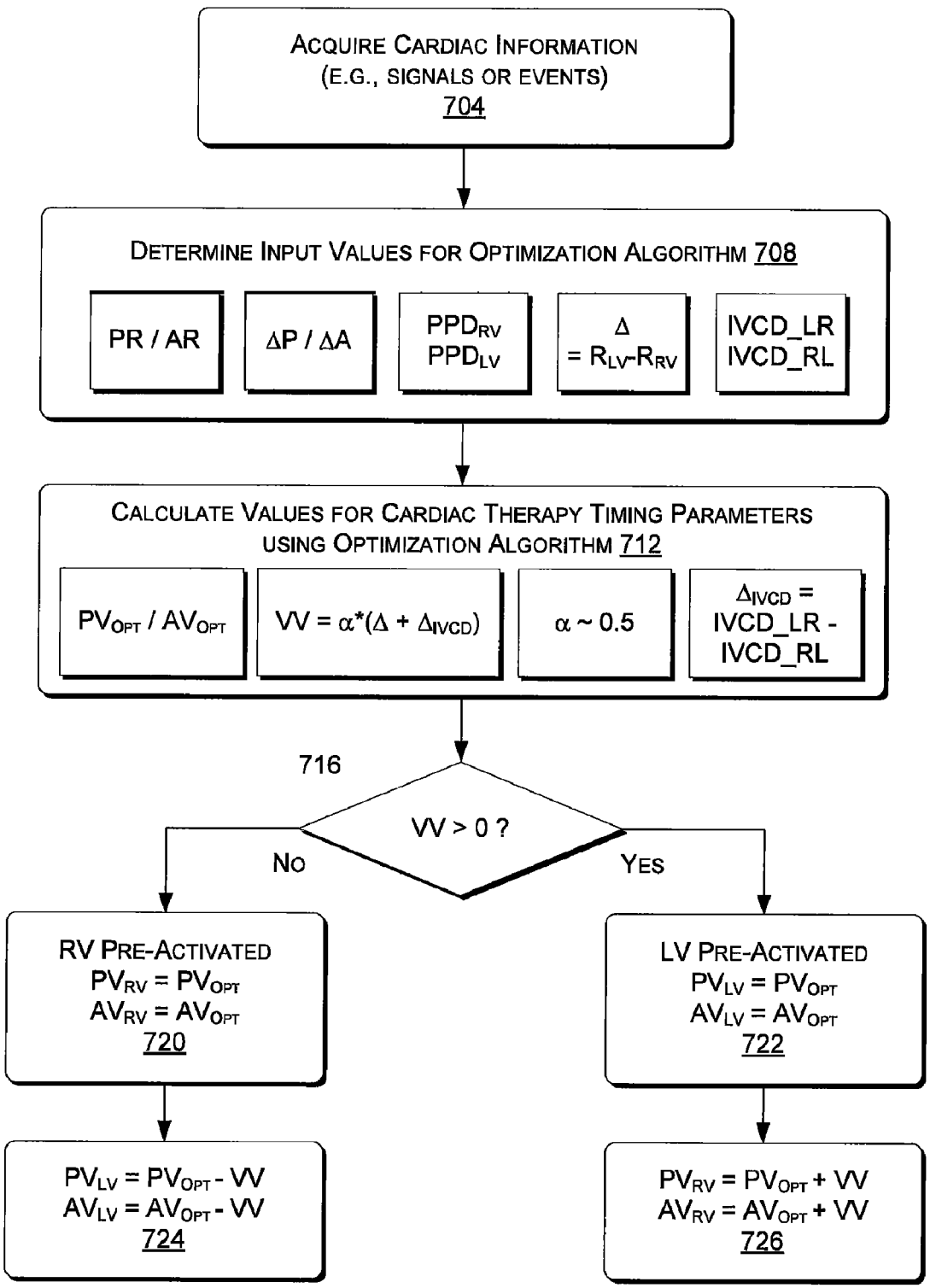
FIG. 7 is a block diagram of an exemplary method for optimizing one or more cardiac pacing parameters.

Various examples discuss parameter optimization (e.g., for CRT and/or bi-ventricular pacing or, more generally, pacing that may use more than one stimulation site). FIG. 7 shows various aspects of parameter optimization techniques.

Various delays or parameters discussed herein include:
PP, AA Interval between successive atrial events
PV Delay between an atrial event and a paced ventricular event
$PV_{optimal}$ Optimal PV delay
$PV_{RV}$ PV delay for right ventricle
$PV_{LV}$ PV delay for left ventricle
AV Delay for a paced atrial event and a paced ventricular event
$AV_{optimal}$ Optimal AV delay
$AV_{RV}$ AV delay for right ventricle
$AV_{LV}$ AV delay for left ventricle
Δ Estimated interventricular delay, e.g., via IEGM, etc.
$\Delta_{programmed}$ Programmed interventricular delay (e.g., a programmed VV delay)
$\Delta_{optimal}$ Optimal interventricular delay, e.g., via hemodynamic sensing/sensor or other cardiac sensing
IVCD-RL Delay between an RV event and a consequent sensed LV event
IVCD-LR Delay between an LV event and a consequent sensed RV event
$\Delta_{IVCD}$ Interventricular conduction delay
ΔP, ΔA Width of an atrial event
DD, AD Interval between end of an atrial wave (e.g., P or A wave) and beginning of a R or QRS complex or other appropriate point
ΔDD, ΔAD $DD_{LV}$-$DD_{RV}$ or $AD_{LV}$-$AD_{RV}$
PPD Paced propagation delay (e.g., time from delivery of stimulation to an evoked response or feature of an evoked response)

FIG. 7 shows a block diagram of an exemplary method 700. The method 700 commences in an acquisition block 704 that acquires cardiac information. Cardiac information may be in the form of signals, events or a combination of signals and events. For example, a detection algorithm may detect an atrial event and a ventricular event and note a time for each of these events. With respect to signals, the acquisition block 704 may acquire electrograms that can be analyzed after their acquisition for any of a variety of features (e.g., a maximum slope as indicative of an evoked response, etc.).

In the example of FIG. 7, the method 700 includes a determination block 708 that determines input values for an optimization algorithm that can optimize timing parameters for delivery of cardiac therapy such as CRT. The input values shown in FIG. 7 include PR/AR, ΔP/ΔA, $PPD_{RV}$/$PPD_{LV}$, Δ, IVCD_LR and IVCD_RL.

According to the method 700, a calculation block 712 calculates values for cardiac therapy timing parameters using the optimization algorithm. While the example of FIG. 7 refers to an optimization algorithm, programmer or device based software, or a look-up table may be used to determine the values of block 712. As indicated, the calculation block 712 calculates an optimum value for the parameter PV or AV (e.g., $PV_{opt}$ or $AV_{opt}$) and, for bi-ventricular pacing, it calculates an optimum value for VV. For example, VV may be calculated using the following equation: $VV=\alpha*(\Delta+\Delta_{IVCD})$ where α is a parameter assigned a value based on experience, patient performance data, etc. In practice, a value for α of about 0.5 has been used with good results.

Upon calculation of a value for the parameter VV, the method 700 enters a decision block 716 that decides if VV exceeds zero. The decision made by the decision block 716 dictates whether ventricular pacing should occur in first in the right ventricle or first in the left ventricle. In FIG. 7, if VV does not exceed zero then the right ventricle is paced first, as indicated in a block 720 "RV Pre-Activated" or "RV Master and LV Slave". However, if VV does exceed zero then the left ventricle is paced first, as indicated in a block 722 "LV Pre-Activated" or "LV Master and RV Slave". In either instance, a block follows 724 or 726, respectively, that calculates the PV or AV timing of the other ventricle based on VV. The various signs used in the method 700 rely on convention and may differ where the equations for Δ and $\Delta_{IVCD}$ differ.

Referring again to the parameter α, a comparison between Δ and $\Delta_{programmed}$ or $\Delta_{optimal}$ can indicate a difference between a current cardiac therapy or state and a potentially better cardiac therapy or state. For example, consider the following equation:

$$\alpha=\Delta_{optimal}/\Delta$$

where α is an optimization parameter. Various echocardiogram and tissue Doppler image technique can be used to determine patient specific α. However echocardiographic studies indicate that the parameter α is typically about 0.5. The use of such an optimization parameter is optional. The parameter α may be used as follows:

$$VV=\alpha*(\Delta+\Delta_{IVCD})$$

If a parameter such as the aforementioned a parameter is available, then such a parameter is optionally used to further adjust and/or set one or more delays, as appropriate.

In many instances, heart condition will affect $AR_{RV}$ and $AR_{LV}$, (or $PR_{RV}$ and $PR_{LV}$) and IVCD (e.g., IVCD-RL and/or IVCD-LR), which, in turn, may affect an existing optimal VV delay setting. Various exemplary methods, devices, systems, etc., include triggering of an algorithm to update an existing optimal VV delay according to a predetermined time or event period or activity sensors for exercise, resting, etc. An exemplary device may include a learning method that learns based on differences in conduction times (e.g., $AR_{RV}$ and $AR_{LV}$, IVCD, etc.) such that parameters associated with different heart demands can be stored. The exemplary learning method may then extract such learned or other parameters to set an optimal VV delay.

In the aforementioned learning example, if the device learns on the basis of different cardiac demands, the device may adjust AV delay and/or VV delay and/or learn a new AV delay and/or VV delay upon a change in cardiac demand. According to this example, use of external measurement or sensing equipment (e.g., echocardiogram, etc.) is optional.

Further, use of internal measurement or sensing equipment for sensing pressure or other indicators of hemodynamic performance is optional. Again, adjustment and learning may rely on IEGM information and/or cardiac other rhythm information.

An exemplary method relies on an atrial to right ventricular conduction time, an atrial to left ventricular conduction time and a cc parameter, for example, as described above, to determine an optimal AV delay and/or VV delay. Another exemplary method relies on an atrial to right ventricular conduction time, an atrial to left ventricular conduction time and a limit that may be used to decide whether one or more of the conduction times are acceptable. In these examples, an interventricular conduction time may be used in lieu of an atrial to ventricular conduction time, for example, where ventricular activity originates with a common atrial event.

According to various exemplary methods, devices, systems, etc., information acquired (e.g., sensed, detected and/or determined) may be used to diagnose cardiac condition. For example, an exemplary method may track AV delays and/or VV delays over time. Such information may then be used to determine subsequent therapy.

Various exemplary methods, devices, systems, etc., include determining an optimal interventricular delay (e.g., $\Delta_{optimal}$) using a modality such as an echocardiogram. While an internal echocardiogram or implantable hemodynamic sensors may be available or become available and be able to measure such optimal delays for a variety of patient circumstances (e.g., sleep, exercise, etc.), an exemplary method, device, system, etc., includes use of one or more internal sensors to measure and/or update such an optimal delay and/or to determine values for one or more parameters related to an optimal delay. For example, a blood pressure sensor (e.g., aortic arch, left atrium, etc.) may be used to determine or to update an optimal delay. Further, information may be collected over a period of time to determine heart condition (e.g., deterioration, improvement, etc.).

In general, an optimal interventricular delay will change as demand and/or heart conditions change. Thus, an exemplary method may determine an optimal interventricular delay during sleep on a nightly, a weekly or some other basis. Such an exemplary method may determine an optimal interventricular delay within a matter of minutes (e.g., approximately 5 heart beats). Such an exemplary method may be triggered according to a change in heart rate or some other parameter related to heart condition. Over time or at time of programming, an exemplary device may store one or more optimal interventricular delays as a function of heart rate, heart condition, etc., and then implement a selected delay from the stored delays upon occurrence of a rate, condition, etc., or a change in rate, condition, etc. Such dynamic control of interventricular delay can improve cardiac performance and potentially allow for an improvement in patient quality of life (e.g., allow for a broader range of patient activity). If after some predetermined period of time or upon occurrence of a particular condition, an exemplary device may indicate a need for a more rigorous determination, for example, via an echocardiogram.

Figure 8:
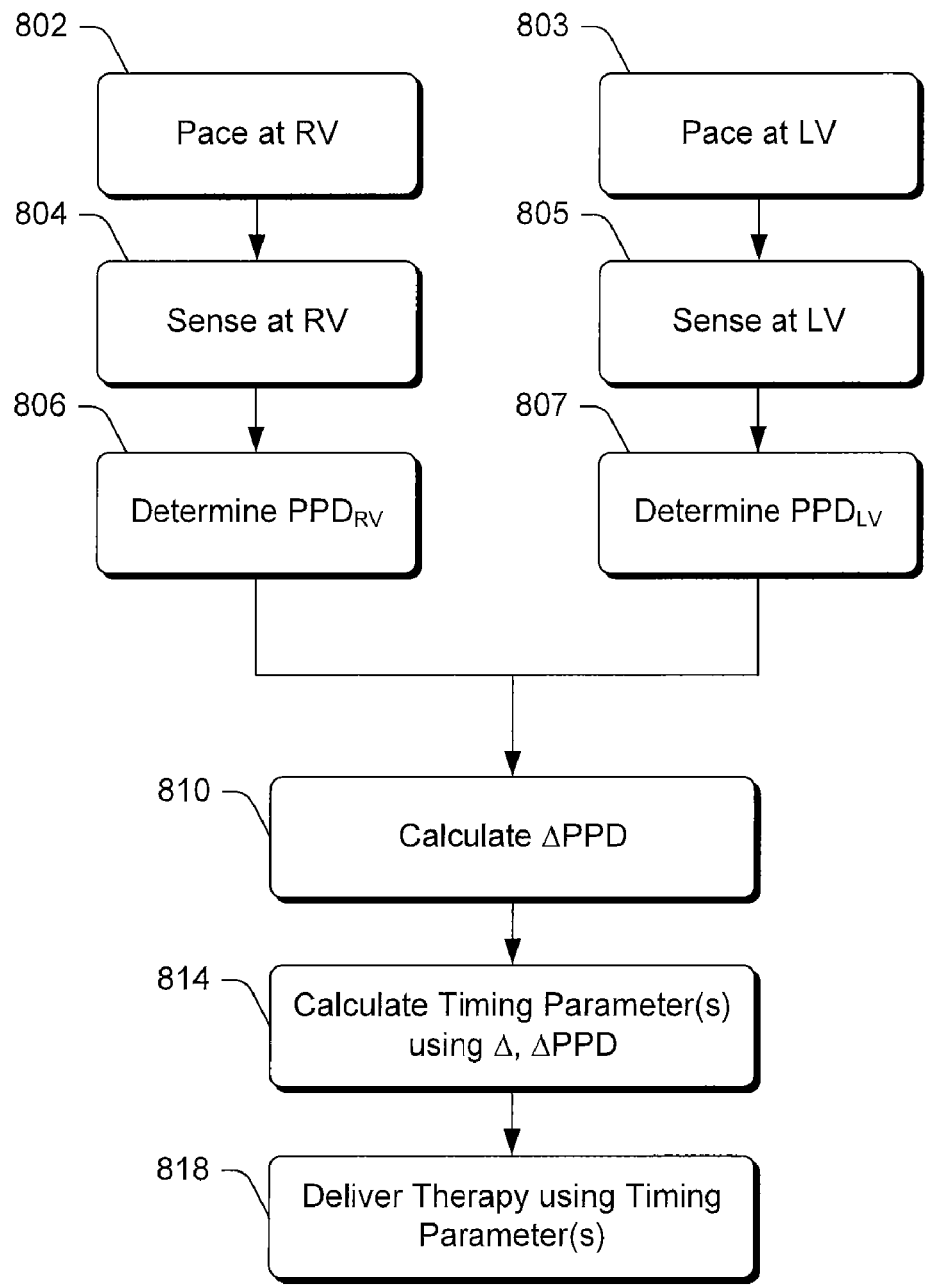
FIG. 8 is a block diagram of an exemplary method for calculating a value for a paced propagation delay parameter.

FIG. 8 shows an exemplary method 800 for calculating a value for the parameter ΔPPD, which can be used in the method 700 of FIG. 7 as an estimate for $\Delta_{IVCD}$ (e.g., as a correction term to determine VV). The method 800 includes a pace block 802 to deliver stimulation at a right ventricular site, a sense block 804 to sense an evoked response to the delivered stimulation and a determination block 806 to determine a PPD for the right ventricular site. Similarly, the method 800 includes a pace block 803 to deliver stimulation at a left ventricular site, a sense block 805 to sense an evoked response to the delivered stimulation and a determination block 807 to determine a PPD for the left ventricular site. In a calculation block 810, the method 800 calculates Δ PPD based on the values determined in blocks 806 and 807. In turn, another calculation block 814 calculates one or more timing parameters using the Δ PPD value and, for example, a value for the parameter Δ (see, e.g., the method 700 of FIG. 7). A delivery block 818 follows that can delivery therapy using the one or more timing parameters.

Figure 9:
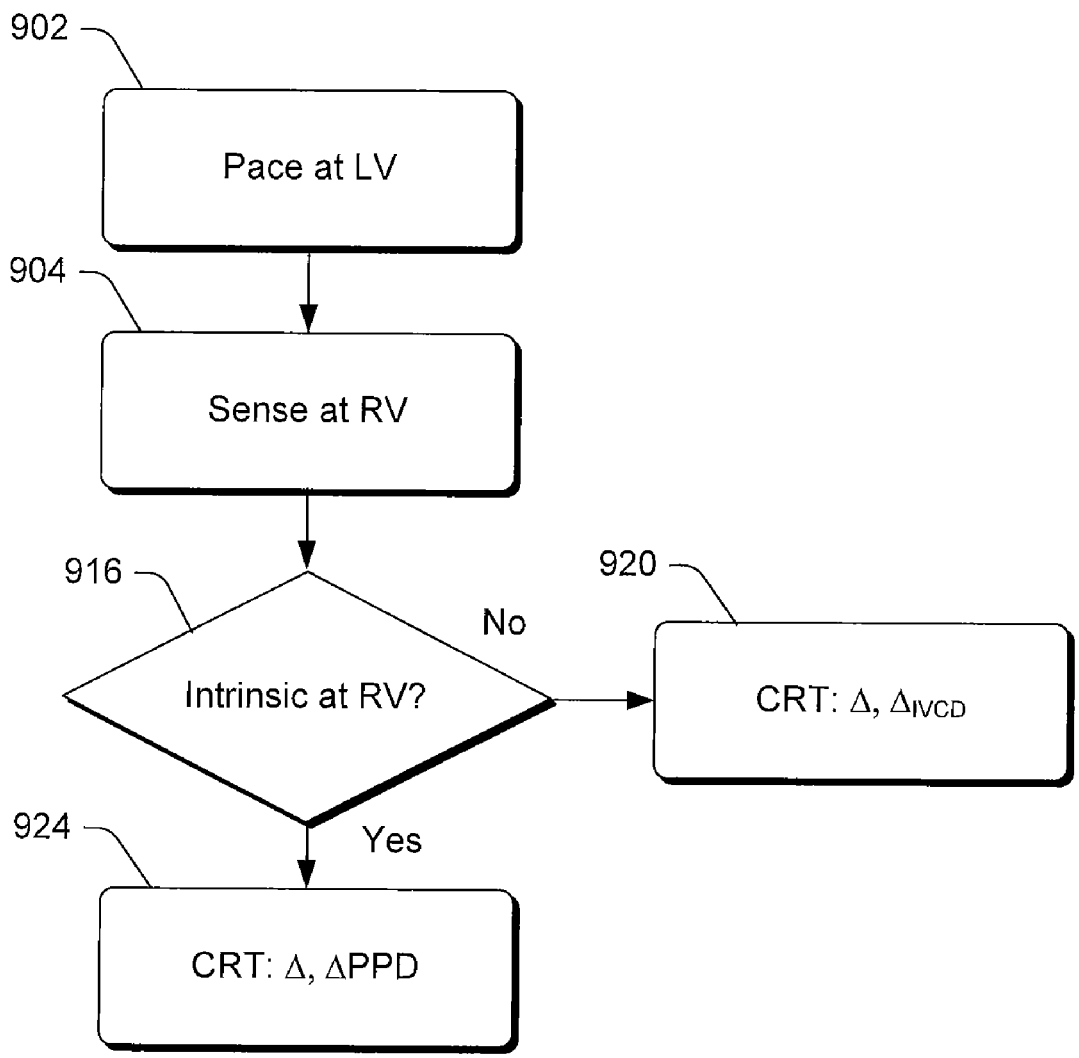
FIG. 9 is a block diagram of an exemplary method for deciding whether to use a paced propagation delay parameter based on sensed cardiac activity.

FIG. 9 shows an exemplary method 900 where a cardiac electrogram is assessed for evidence of intrinsic activity. In a pace block 902 an implantable device such as the device 100 of FIGS. 1 and 2 delivers stimulation energy to a left ventricular site. A sense block 904 follows that senses activity via a right ventricular site. A decision block 916 decides if the sensed activity is intrinsic. If the sensed block 904 sense intrinsic activity prior to activity associated with the left ventricular pace per block 902, then it may not be possible to measure a value for $\Delta_{IVCD}$. Accordingly, the method 900 continues at the CRT block 924 where PPD information is used to determine one or more CRT timing parameters (see, e.g., the method 800 of FIG. 8). Alternatively, if the decision block 916 decides that intrinsic activity was not sensed but rather activity associated with the left ventricular pace, then the method 900 continues in a CRT block 922 where IVCD-LR may be used to aid in determining one or more CRT timing parameters (see, e.g., the method 700 of FIG. 7).

As described herein, an exemplary method may decide whether to use PPD information to determine one or more CRT timing parameters. For example, based on evidence of myocardial damage such as scarring, a method may decide to use PPD information. Such evidence may be acquired by an implantable device or by an external device (e.g., ECG, MRI, echo cardiography, etc.). For electrograms, evidence may include fragmented QRS complexes, which include various RSR' patterns, or other evidence as discussed with respect to FIG. 4. For MRI, evidence may include myocardial profusion images. For an echo cardiography technique, evidence may include myocardial thickness.

Figure 10:
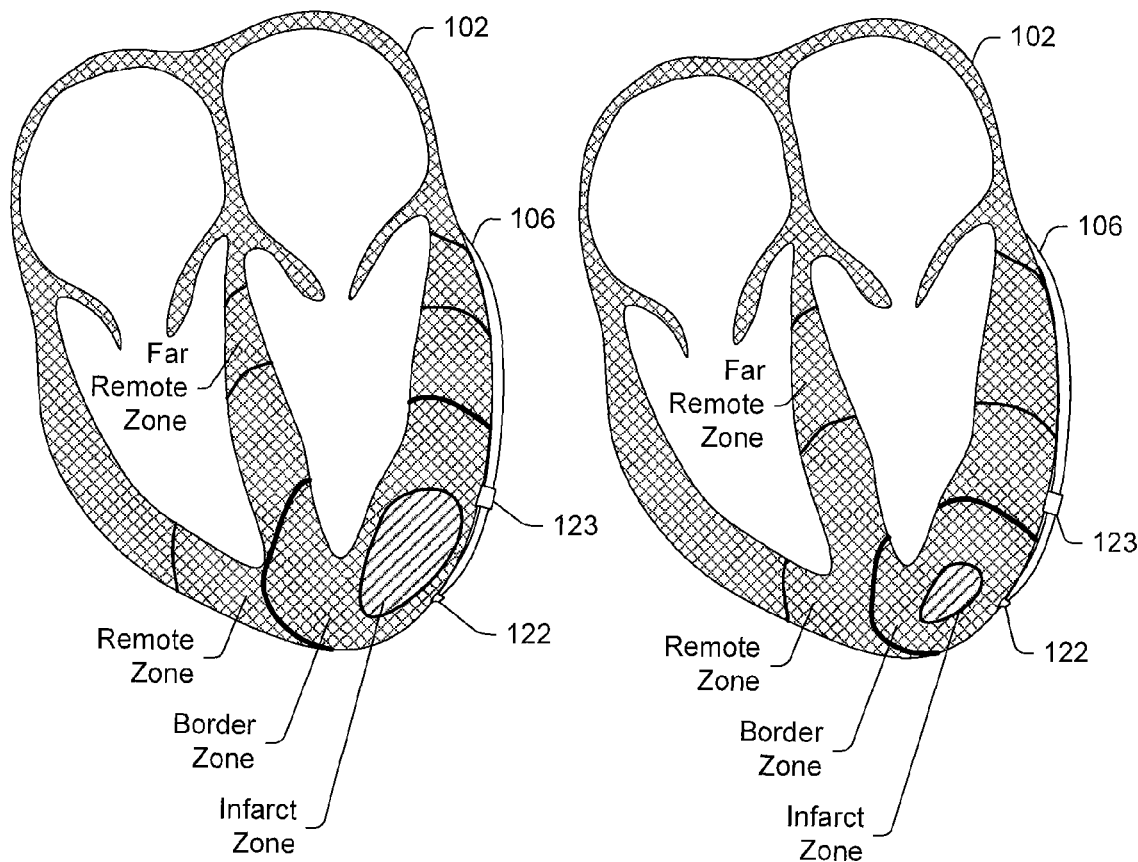
FIG. 10 is a diagram of a heart showing damage at an early time and a later time and how the value of a paced propagation delay parameter may change over time.

FIG. 10 shows an exemplary method 1000 where values for the parameter ΔPPD or underlying PPD information (e.g., $PPD_{LV}$, $PPD_{RV}$) are determined at more than one time to allow for trending or historical analysis. The method 1000 includes acquiring PPD information at an initial time 1010, acquiring PPD information at a later time 1020 and comparing the paced propagation delay information at the two different times 1030. For example, as shown in FIG. 10, the infarct zone has diminished in size from the initial time to the later time. As the left ventricular electrodes 122 and 123 are located proximate the infarct zone, a change may be expected in PPD for the left ventricle ($PPD_{LV}$). For example, the time may decrease as the infarct zone decreases in size. As described herein, PPD information may allow for tracking changes in myocardial tissue as well as for optimizing one or more CRT timing parameters.

Figure 11:
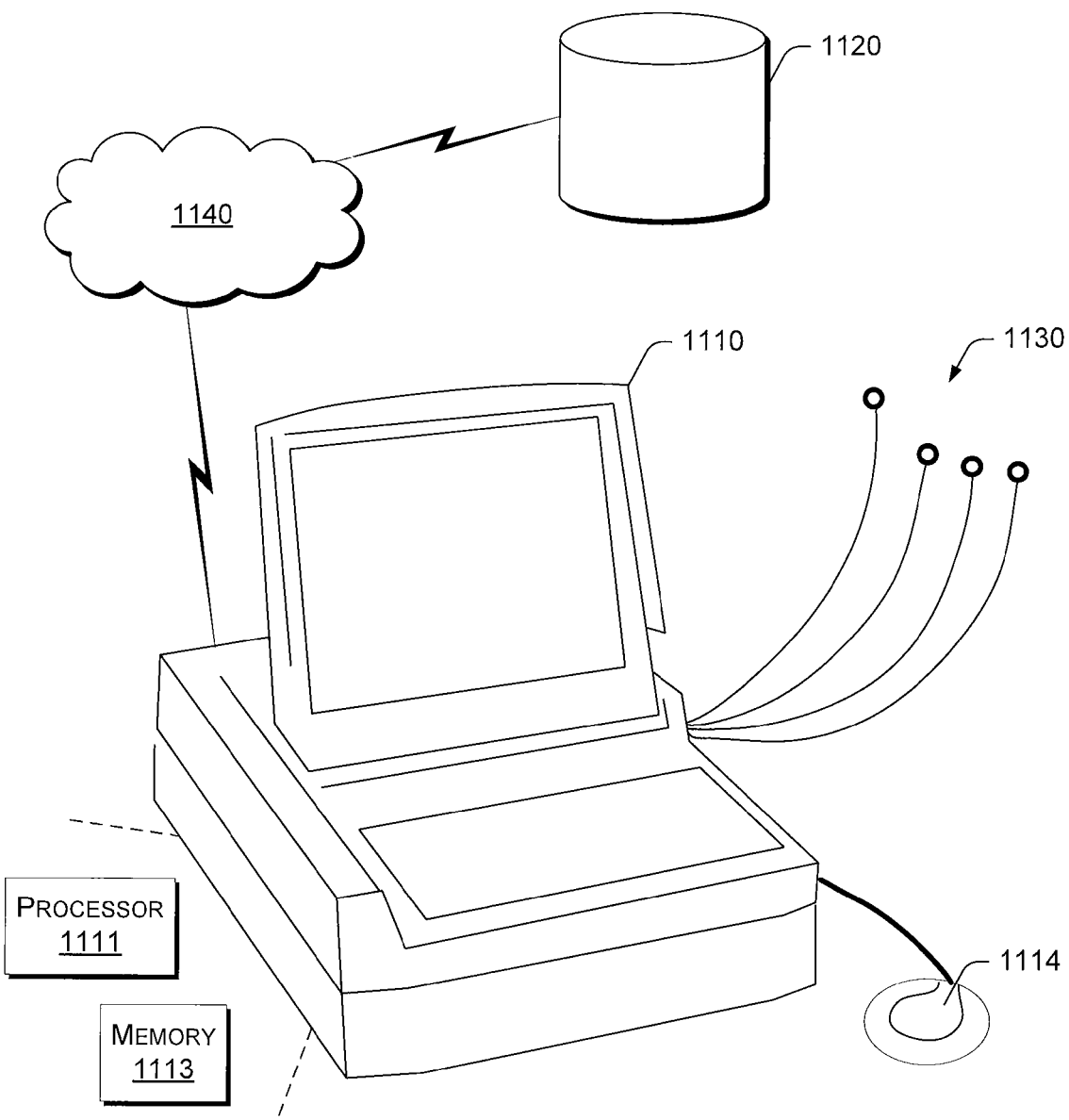
FIG. 11 is a diagram of an exemplary system that includes a programmer configured to communicate with an implantable device.

FIG. 11 shows an exemplary system 1100 that includes a programmer 1110, a database 1120 and a series of leads 1130 for acquiring ECG information. The programmer 1110 includes a processor 1111 and memory 1113. Memory 1113 may be store instructions executable by the processor 1111 to cause the programmer 1110 to perform various actions. The programmer 1110 through the memory 1113, or other techniques, may implement control logic to make decisions regarding algorithms for use in cardiac pacing or other cardiac therapy.

The programmer 1110 may have various features such as, but not limited to, features of the St. Jude Medical 3510 programmer or the MERLIN® programmer (St. Jude Medical, Inc., Sylmar, Calif.). For example, a suitable programmer may optionally have more capabilities with respect to multi-lead ECG acquisition. The programmer 1110 includes a paddle or wand 1114 for communication with an implantable device (e.g., consider the device 100 of FIGS. 1 and 2). For example, the paddle or wand 1114 may include a transmitter for communicating information such as CRT settings to an implantable device and for receiving IEGM or other information generated by an exemplary method. The programmer 1110 may rely on a communications network 1140 to access or to store information in a database 1120 (e.g., model information, ECG information, subject information, CRT device information, etc.). In this example, the programmer 1110 can use the leads 1 130 for acquisition of multi-lead ECG information.

An exemplary computing device includes a processor, an input for receiving electrocardiogram information and control logic operable in conjunction with the processor to determine one or more measures based on the electrocardiogram information and to select one or more cardiac resynchronization therapy settings based at least in part on the one or more measures. Such a device may select a VV delay, an AV delay (or PV delay) or other CRT setting. Such a device optionally includes features of the programmer 1110. For example, the exemplary computing device may include a transmitter (e.g., paddle or wand 1114) to transmit information to an implantable device (e.g., the implantable device 100 of FIGS. 1 and 2). Further, such an implantable device may be configured to deliver cardiac resynchronization therapy. For example, an implantable device may include control logic for bi-ventricular pacing suitable for CRT or left ventricular pacing suitable for CRT.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
delivering stimulation energy via a right ventricular site;
sensing an evoked response caused by the delivered stimulation energy at the right ventricular site;
calculating a paced propagation delay for the right ventricular site ($PPD_{RV}$) wherein the paced propagation delay comprises a time interval between delivery of the stimulation to the right ventricular site and a feature of the corresponding sensed right ventricular evoked response;
delivering stimulation energy via a left ventricular site;
sensing an evoked response caused by the delivered stimulation energy at the left ventricular site;
calculating a paced propagation delay for the left ventricular site ($PPD_{LV}$) wherein the paced propagation delay comprises a time interval between delivery of the stimulation to the left ventricular site and a feature of the corresponding sensed left ventricular evoked response;
determining an interventricular delay time (VV) for delivery of a bi-ventricular pacing therapy based in part on the paced propagation delay for the right ventricular site ($PPD_{RV}$) and the paced propagation delay for the left ventricular site ($PPD_{LV}$); and
calculating a time difference between the paced propagation delay for the right ventricular site and the paced propagation delay for the left ventricular site ($\Delta PPD$) and using this time difference as an estimate for a time difference ($\Delta_{IVCD}$) between an interventricular conduction delay from the left ventricle to the right ventricle (IVCD-LR) and an interventricular conduction delay from the right ventricle to the left ventricle (IVCD-RL).

2. The method of claim 1 further comprising calculating a time difference ($\Delta PPD$) between the paced propagation delay for the right ventricular site and the paced propagation delay for the left ventricular site.

3. The method of claim 1 further comprising determining an atrial to right ventricular interval ($AR_{RV}$ or $PR_{RV}$) and an atrial to left ventricular interval ($AR_{LV}$ or $PR_{LV}$) and determining the interventricular delay time (VV) based in part on the atrial to right ventricular interval ($AR_{RV}$ or $PR_{RV}$) and the atrial to left ventricular interval ($AR_{LV}$ or $PR_{LV}$).

4. The method of claim 3 further comprising determining a time difference ($\Delta$) between the atrial to right ventricular interval ($AR_{RV}$ or $PR_{RV}$) and the atrial to left ventricular interval ($AR_{LV}$ or $PR_{LV}$).

5. The method of claim 1 further comprising attempting to determine an interventricular conduction delay from the left ventricle to the right ventricle (IVCD-LR) or from the right ventricle to the left ventricle (IVCD-RL).

6. The method of claim 5 wherein a failure to determine the interventricular conduction delay from the left ventricle to the right ventricle (IVCD-LR) or from the right ventricle to the left ventricle (IVCD-RL) initiates the determining an interventricular delay time (VV) for delivery of a bi-ventricular pacing therapy based in part on the paced propagation delay for the right ventricular site ($PPD_{RV}$) and the paced propagation delay for the left ventricular site ($PPD_{LV}$).

7. The method of claim 1 further comprising analyzing the interventricular delay time (VV) and the paced propagation delay for the left ventricular site ($PPD_{LV}$) with respect to time.

8. The method of claim 1 further comprising analyzing the interventricular delay time (VV) and the paced propagation delay for the right ventricular site ($PPD_{RV}$) with respect to time.

9. The method of claim 1 further comprising analyzing the interventricular delay time (VV), the paced propagation delay for the right ventricular site ($PPD_{RV}$) and the paced propagation delay for the left ventricular site ($PPD_{RV}$) with respect to time.

10. The method of claim 1 wherein evidence of myocardial damage initiates the determining an interventricular delay time (VV) for delivery of a bi-ventricular pacing therapy based in part on the paced propagation delay for the right ventricular site and the paced propagation delay for the left ventricular site.

11. A method comprising:
delivering stimulation to one ventricle;
sensing activity in the other ventricle;
deciding if the sensed activity corresponds to intrinsic activity or activity associated with the delivered stimulation;
if the sensed activity corresponds to intrinsic activity, calling for determining an interventricular delay time (VV) for delivery of a bi-ventricular pacing therapy based in part on a paced propagation delay for the right ventricular site and a paced propagation delay for the left ventricular site wherein a paced propagation delay comprises a time interval between delivery of stimulation to a site and a feature of a waveform of a corresponding evoked response; and calculating a time difference between the paced propagation delay for the right ventricular site and the paced propagation delay for the left ventricular site (ΔPPD) and using this time difference as an estimate for a time difference ($\Delta_{IVCD}$) between an interventricular conduction delay from the left ventricle to the right ventricle (IVCD-LR) and an interventricular conduction delay from the right ventricle to the left ventricle (IVCD-RL).

12. The method of claim 11 wherein the delivering delivers stimulation energy to the left ventricle and wherein the sensing senses activity in the right ventricle.

13. The method of claim 11 wherein the delivering delivers stimulation energy to the right ventricle and wherein the sensing senses activity in the left ventricle.

14. A method comprising:
acquiring one or more cardiac electrograms;
analyzing the one or more cardiac electrograms for evidence of myocardial damage;
if evidence of myocardial damage exists, calling for determining an interventricular delay time (VV) for delivery of a bi-ventricular pacing therapy based in part on a paced propagation delay for the right ventricular site and a paced propagation delay for the left ventricular site wherein a paced propagation delay comprises a time interval between delivery of stimulation to a site and a feature of a waveform of a corresponding evoked response; and
calculating a time difference between the paced propagation delay for the right ventricular site and the paced propagation delay for the left ventricular site (ΔPPD) and using this time difference as an estimate for a time difference ($\Delta_{IVCD}$) between an interventricular conduction delay from the left ventricle to the right ventricle (IVCD-LR) and an interventricular conduction delay from the right ventricle to the left ventricle (IVCD-RL).

15. The method of claim 14 wherein the one or more cardiac electrograms comprise one or more IEGMs.

16. The method of claim 14 wherein the one or more cardiac electrograms comprise one or more surface ECGs.

17. An implantable device comprising:
memory;
a processor;
a left ventricular pacing lead;
a right ventricular pacing lead; and
control logic to deliver stimulation energy via the left ventricular pacing lead and the right ventricular pacing lead according to an interventricular delay (VV) based in part on a paced propagation delay associated with the left ventricular pacing lead ($PPD_{LV}$) and a paced propagation delay associated with the right ventricular pacing lead ($PPD_{RV}$) wherein a paced propagation delay (PPD) comprises a time interval between delivery of stimulation to a site and a feature of a waveform of a corresponding evoked response; and
wherein the control logic is adapted to calculate a time difference between the paced propagation delay for the right ventricular site and the paced propagation delay for the left ventricular site (ΔPPD) and use this time difference as an estimate for a time difference ($\Delta_{IVCD}$) between an interventricular conduction delay from the left ventricle to the right ventricle (IVCD-LR) and an interventricular conduction delay from the right ventricle to the left ventricle (IVCD-RL).

18. The device of claim 17 further comprising control logic to decide whether to determine an interventricular delay (VV) based in part on a paced propagation delay associated with the left ventricular pacing lead ($PPD_{LV}$) and a paced propagation delay associated with the right ventricular pacing lead ($PPD_{RV}$).

19. The device of claim 18 wherein the control logic to decide comprises control to attempt to determine an interventricular conduction delay from the left ventricle to the right ventricle (IVCD-LR) or from the right ventricle to the left ventricle (IVCD-RL).

* * * * *